US010098916B2

(12) United States Patent
Seme et al.

(10) Patent No.: US 10,098,916 B2
(45) Date of Patent: Oct. 16, 2018

(54) **STRAINS OF THE GENUS *LACTOBACILLUS* AND USE THEREOF**

(71) Applicant: MEDIS, d.o.o., Ljubljana-Crnuce (SI)

(72) Inventors: Helena Seme, Grosuplje (SI); Stefan Fujs, Kisovec (SI); Kresimir Gjuracic, Zagreb (HR); Hrvoje Petkovic, Ljubljana (SI); Gregor Kosec, Ljubljana (SI); Mateja Stempelj, Ljubljana (SI); Karmen Svigelj, Rakek (SI); Tone Strnad, Ljubljana (SI)

(73) Assignee: MEDIS, D.O.O., Ljubljana-Crnuce (SI)

( * ) Notice: Subject to any disclaimer, the term of this patent is extended or adjusted under 35 U.S.C. 154(b) by 28 days.

(21) Appl. No.: 15/105,876

(22) PCT Filed: Dec. 19, 2014

(86) PCT No.: PCT/SI2014/000079
§ 371 (c)(1),
(2) Date: Jun. 17, 2016

(87) PCT Pub. No.: WO2015/099617
PCT Pub. Date: Jul. 2, 2015

(65) Prior Publication Data
US 2016/0375069 A1    Dec. 29, 2016

(30) Foreign Application Priority Data

Dec. 23, 2013 (SI) .................................. P-201300443

(51) Int. Cl.
| | |
|---|---|
| *C12N 1/20* | (2006.01) |
| *A61K 35/747* | (2015.01) |
| *A23L 33/135* | (2016.01) |
| *C12R 1/25* | (2006.01) |
| *A23K 10/18* | (2016.01) |
| *A61K 35/00* | (2006.01) |

(52) U.S. Cl.
CPC ............ *A61K 35/747* (2013.01); *A23K 10/18* (2016.05); *A23L 33/135* (2016.08); *C12N 1/20* (2013.01); *C12R 1/25* (2013.01); *A23V 2002/00* (2013.01); *A23Y 2220/67* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 5,474,932 A | 12/1995 | Bengmark et al. | |
| 5,587,314 A | 12/1996 | Bengmark et al. | |
| 5,591,428 A | 1/1997 | Bengmark et al. | |
| 2012/0225465 A1* | 9/2012 | Pimentel | C12P 7/10 |
| | | | 435/165 |
| 2013/0101566 A1 | 4/2013 | Mazo et al. | |
| 2015/0328267 A1 | 11/2015 | Wyrobnik et al. | |

FOREIGN PATENT DOCUMENTS

| | | |
|---|---|---|
| EP | 0 554 418 B1 | 3/1998 |
| EP | 1 374 878 A1 | 1/2004 |
| EP | 1 268 808 B1 | 12/2006 |
| WO | 2008/001676 A1 | 1/2008 |
| WO | 2011/092261 A1 | 8/2011 |
| WO | 2011/095339 A1 | 8/2011 |

OTHER PUBLICATIONS

NRRL ("Lactobacillus plantarum database" and "B-4496 strain" provided, available at nrrl.ncaur.usda.gov/cgi-bin/usda/process.html, accessed Aug. 1 2017, NRRL, Peoria IL).*
Pederson, (A Study of the Species *Lactobacillus plantarum* (Orla-Jensen) Bergey Et Al, Journal of Bacteriology, vol. 31. Issue 3, 217-224).*
Sorensen, ("Enhancing the Sweetness of yoghurt through metabolic remodeling of carbohydrate metabolism in *Streptococcus thermophilus* and *Lactobacillus delbrueckii* subsp. bulgaricus", Applied and Environmental Microbiology, 82(12), 3683-3692, Jun. 2016),.*
International Search Report issued in PCT/SI2014/000079; dated Apr. 30, 2015.
Soren Nobaek et al.; "Alteration of Intestinal Microflora Is Associated With Reduction in Abdominal Bloating and Pain in Patients With Irritable Bowel Syndrome"; The American Journal of Gastroenterology; 2000; pp. 1231-1238; vol. 95; No. 5; Elsevier Science Inc.
Sirikhwan Tinrat et al.; "Isolation and characterization of *Lactobacillus salivarius* MTC 1026 as a potential probiotic"; The Journal of General and Applied Microbiology; 2011; pp. 365-378; vol. 57; No. 6.

* cited by examiner

*Primary Examiner* — Robert J Yamasaki
*Assistant Examiner* — Charles Zoltan Constantine
(74) *Attorney, Agent, or Firm* — Buchanan Ingersoll & Rooney PC (57) ABSTRACT

This invention provides novel strains of the genus *Lactobacillus* which can be used to produce pharmaceutical products with probiotic properties for human or veterinary use. The strains of this invention possess metabolic features that are particularly suitable for treatment of disorders related to lactose malabsorption and intolerance, fructose malabsorption and intolerance, and bloating.

8 Claims, 1 Drawing Sheet
Specification includes a Sequence Listing.

Figure 1: Growth curves of strain *Lactobacillus plantarum* KR6 on MRS medium with different sugars (━◆━ without sugar, ━■━ glucose, ━▲━ fructose, ━●━ raffinose, ━━ lactose).

SEQUENCE LISTING

<160> NUMBER OF SEQ ID NOS: 1

<210> SEQ ID NO 1
<211> LENGTH: 634
<212> TYPE: DNA
<213> ORGANISM: Lactobacillus plantarum
<220> FEATURE:
<223> OTHER INFORMATION: 16 S rRNA gene partial sequence

<400> SEQUENCE: 1
gcggcgtgcc taatacatgc aagtcgaacg aactctggta ttgattggtg cttgcatcat      60

-continued

```
gatttacatt tgagtgagtg gcgaactggt gagtaacacg tgggaaacct gcccagaagc      120
gggggataac acctggaaac agatgctaat accgcataac aacttggacc gcatggtccg      180
agcttgaaag atggcttcag ctatcactt  tggatggtcc cgcggcgtat tagctagatg      240
gtggggtaac ggctcaccat ggcaatgata cgtagccgac ctgagagggt aatcggccac      300
attgggactg agacacggcc caaactccta cgggaggcag cagtagggaa tcttccacaa      360
tggacgaaag tctgatggag caacgccgcg tgagtgaaga agggtttcgg ctcgtaaaac      420
tctgttgtta aagaagaaca tatctgagag taactgttca ggtattgacg gtatttaacc      480
agaaagccac ggctaactac gtgccagcag ccgcggtaat acgtaggtgg caagcgttgt      540
ccggatttat tgggcgtaaa gcgagcgcag gcggtttttt aagtctgatg tgaaagcctt      600
cggctcaacc gaagaagtgc atcggaaact ggga                                 634
```

STRAINS OF THE GENUS *LACTOBACILLUS* AND USE THEREOF

TECHNICAL FIELD

The present invention relates to the fields of medicine, microbiology and nutrition and, particularly, to a novel probiotic composition. Particularly, new strains of genus *Lactobacillus* have been isolated and combined in a formulation useful in the treatment of lactose malabsorption and intolerance, fructose malabsorption and intolerance, and bloating.

TECHNICAL PROBLEM

The technical problem to be solved by the proposed invention is to use novel strains of genus *Lactobacillus* for the treatment of lactose malabsorption and intolerance, fructose malabsorption and intolerance, and bloating. The strains according to this invention consume fructose, lactose and raffinose while not producing gas. Furthermore, mutants of one of the strains of this invention are resistant to 2-deoxyglucose and able to consume fructose, lactose and raffinose in parallel with glucose, when several sugars are present in the growth medium.

BACKGROUND OF THE INVENTION

Lactic acid bacteria are Gram positive, non-sporulating bacteria, tolerant to acid pH with facultative anaerobic characteristics. They are a heterogeneous group of bacteria which are naturally present in nutrient rich environments. Their efficient use of nutrients and production of lactic acid during growth are important selective advantages. Many species are used for manufacturing and preservation of fermented feed and food, but they are also common among bacteria populating gastrointestinal tract of humans and animals. The genus *Lactobacillus* is the largest among lactic acid bacteria and consists of over 190 species, though its number is still increasing. They occur as rods or coccobacilli, with guanine and cytosine composition of the genome usually below 50%. Generally, they are the most acid tolerant microorganisms among lactic acid bacteria, so they are terminators of spontaneous lactic fermentations such as silage or vegetable fermentations. According to metabolism, they can be divided into three groups. A first group is obligately homofermentative lactobacilli which produce lactic acid as a primary by-product from carbohydrate fermentation. They cannot ferment pentoses and gluconate and do not produce $CO_2$. A second group is facultatively heterofermentative lactobacilli which cannot produce $CO_2$ from glucose, because they use the same pathway as homofermentative lactobacilli but they can produce $CO_2$ from gluconate. They are the only group which can ferment pentoses into lactic and acetic acid. A third group is obligately heterofermentative lactobacilli which produce $CO_2$ when fermenting glucose and gluconate and cannot ferment pentoses. They also produce lactic acid when fermenting glucose but also other products such as acetic acid, ethanol and carbon dioxide. *Lactobacillus plantarum* was one of the first taxa described in the genus and belong to a group of facultatively heterofermentative *Lactobacillus*. Species is commonly found in plant material, but also in dairy products, human colon, sewage and many other environments. This flexibility also indicates that the species is genetically and phenotypically heterogenous with one of the largest genomes in the group of lactic acid bacteria. A wide variety of *Lactobacillus* strains have a long history of apparent safe use. Therefore the whole taxonomical unit of *Lactobacillus* has GRAS (generally recognised as safe) or QPS (qualified presumption of safety) status, thus *Lactobacillus* strains can be used in industrial food and feed fermentation and due to positive effects on digestive system also as probiotics. Probiotics are defined as live microorganisms which, when administered in adequate amounts, confer a beneficial impact on the host. Some of those beneficial effects are regulation of gut microbiota, stimulation of immune system, reducing risks of certain diseases and reducing symptoms of lactose intolerance and other malabsorptions. It is desired that probiotic is capable of adhesion to intestinal epithelium, and can thus be present in the gut for a longer period of time.

Many dietary sugars are not efficiently absorbed from the human intestine into the blood stream. Unabsorbed sugars are then digested in the large intestine leading to production of large amounts of gas which may cause symptoms of pain, abdominal bloating, flatulence, and diarrhea. In case of many plant oligosaccharides (e.g. raffinose) this is caused by natural inability of the human digestive system to digest these sugars. Oligosaccharides consist of three to ten monosaccharides connected with an alpha-galactoside bond, often attached to proteins or lipids. Bacteria can digest those oligosaccharides, because they possess the enzyme alpha-galactosidase which cleaves polysaccharides into monosaccharides. Smaller units can be absorbed by the human digestive tract. On the other hand, malabsorption is defined as defective or inadequate absorption of nutrients from the intestinal tract. Malabsorption of fructose has 30 to 40% incidence in Europe and is gut mucosal abnormality when small intestine's enterocytes have impaired fructose carriers. The result is increased fructose concentration in the entire intestine which leads to increased osmotic pressure and reduced water absorption. Fructose is digested by colonic bacteria into hydrogen, carbon dioxide and methane. An abnormal increase in hydrogen is detectable with a hydrogen breath test. Symptoms for fructose malabsorption include bloating, stomach pain, spasms, flatulence and diarrhea. The symptoms of lactose intolerance (lactose malabsorption) are the same as in fructose malabsorption and detection of both is the same. Lactose intolerance is inability to digest lactose due to insufficient levels of intestinal lactase in adult age. It is rarely absolute and can vary between individuals. Undigested lactose travels into the large intestine, where it is digested by colon bacteria which produce gas—the main reason for bloating and stomach pain.

EP0554418 discloses the strain of *Lactobacillus plantarum* 299v which has the ability to colonize and become established on intestinal mucosa thereby demonstrating the usefulness of *L. plantarum* as components of probiotic preparations.

WO2011/092261 discloses several *Lactobacillus* strains including *Lactobacillus plantarum* CECT 7485 and CECT7484, which are effective in the treatment of bowel inflammation, e.g. for the treatment of symptoms commonly denoted as inflammatory bowel disease (IBD) and irritable bowel syndrome (IBS). These strains also possess all other beneficial properties which make them suitable for use in probiotic preparations, such as absence of antibiotic resistance, resistance to conditions in gastrointestinal environment and adhesion to intestinal epithelium.

EP1268808 discloses *Lactobacillus casei* strain defective in carbon catabolism regulation for use in fermentation of food and feed products. This strain is resistant to 2-deoxyglucose which allows it to consume different carbon sources simultaneously.

EP1374878 discloses a method of preventing or alleviating symptoms of malabsorption by administering a dietary supplement containing bacterial cells. Dietary supplement comprises at least $10^6$ metabolically active cells of the genus *Propionibacterium*, at least 0.5 g of a prebiotic and/or at least $10^6$ metabolically active homofermentative cells of the genus *Lactobacillus* and/or at least $10^6$ metabolically active cells of the genus *Bifidobacterium*.

A study by Rampengan et al (2010) (Southeast Asian J Trop Med Pub Health, 2010, 41: 474-481) observed similar efficiency of live or killed probiotics in children with lactose intolerance. When probiotics were consumed for two weeks, the hydrogen in their breath was reduced.

Another study performed by Di Stefano et al (2004) (J Clin Gastroenterol., 2004, 38 Suppl: S102-103) studied the effect of probiotic *Lactobacillus rhamnosus* LGG on functional abdominal bloating. LGG proved to be more effective than placebo in reducing the severity of symptoms.

A study by Nobaek et al (2000) (Am J Gastroenterol. 2000, 95: 1231-1238) compared patients with irritable bowel syndrome receiving *Lactobacillus plantarum* 299v DSM 9843 for four weeks and a placebo group. Flatulence was rapidly and significantly reduced in the test group receiving the probiotic strain. At the 12 month follow-up, the test group maintained a better overall gastrointestinal function than control patients.

Further on, WO2011/095339 discloses a composition comprising a lactase enzyme and lactase containing strains of the genus *Lactobacillus* for alleviation of the symptoms of lactose intolerance.

In another example, WO2008/001676 discloses a lactic acid bacterium capable of ameliorating lactose intolerance, characterized by selecting a bacterium having an enhanced enteroadherence property and an enhanced lactose-degrading enzyme activity from lactic acid bacteria belonging to the genus *Lactobacillus*.

However, a strain of the genus *Lactobacillus* able to rapidly consume carbohydrates, most frequently involved in bloating, fructose, lactose and raffinose, without producing gas and suitable for preparation of probiotic compositions has so far not been described. Therefore, the exploitation of such metabolic capabilities (e.g. consumption of selected components of foodstuffs and their conversion to biomass or end products without health-detrimental effects) of *Lactobacillus* strains for conferring health beneficial effects has so far not been envisioned. Thus the currently used probiotic preparations and strains do not, when they arrive into the intestine, reduce the symptoms of lactose intolerance or fructose malabsorption or bloating by consuming fructose, lactose and raffinose and converting them into non-gaseous metabolites.

SUMMARY OF THE INVENTION

This invention provides strains of *Lactobacillus* which in the presence of, independently, fructose, lactose or raffinose as replacement for an equal mass of glucose in standard MRS medium grows with at least 0.7 of growth rate which is achieved if glucose is present in the medium.

Additionally, the strains of this invention grow in the MRS medium containing 25% of a peptone and yeast extract with a growth rate of at least 0.7 of the growth rate observed in the standard MRS medium.

Furthermore, the cultivation of this strain in the MRS medium does not lead to generation of gas.

In a further aspect of the present invention, said *Lactobacillus* strains cannot grow in the presence of antibiotics ampicillin (more than 4 mg/l), gentamicin (more than 32 mg/l), kanamycin (more than 64 mg/l), streptomycin (more than 64 mg/l), erythromycin (more than 1 mg/l), clindamycin (more than 1 mg/l), tetracycline (more than 32 mg/l), chloramphenicol (more than 8 mg/l) or quinupristin+dalfopristin (more than 4 mg/l) on agar plates consisting of 90% Mueller Hinton Agar (0.2% beef extract, 1.75% acid digest of casein, 0.15% starch, 1.7% agar) and 10% MRS agar with pH adjusted to 6.7.

This invention refers particularly to a new *Lactobacillus* strain which has been deposited according to the Budapest Agreement at the Leibniz-Institut DSMZ—Deutche Sammlung von Mikoorganismen and Zellkulturen GmbH at Inhoffenstraße 7B, 38124 Braunschweig, Germany on Oct. 17, 2013 under accession number DSM 27870. This is *Lactobacillus plantarum* DSM 27870, hereinafter also named "KR6" and "*Lactobacillus plantarum* KR6". According to the Budapest Agreement, all restrictions on the availability to the public of the material so deposited will be irrevocably removed upon the granting of a patent.

This invention also refers to the progeny of the strain *Lactobacillus plantarum* DSM 27870 obtained either by methods of classical selection, possibly assisted by mutagenesis, or methods of metabolic engineering.

In one embodiment the strains of this invention have an additional characteristic that they are resistant to 2-deoxyglucose. Such strains are particularly beneficial as they do not present catabolic repression by glucose and they consume substantial amounts of lactose, fructose or raffinose from the growth medium, in which glucose is also present.

In this embodiment, this invention refers to the progeny of *Lactobacillus plantarum* DSM 27870 which can be obtained by methods of classical mutagenesis and selection or by methods of genetic engineering. Particularly, this invention refers particularly to a *Lactobacillus* strain which has been deposited according to the Budapest Agreement at the Leibniz-Institut DSMZ—Deutche Samm lung von Mikoorganismen and Zellkulturen GmbH at Inhoffenstraße 7B, 38124 Braunschweig, Germany on Oct. 30, 2013 under accession number DSM 26329. This is *Lactobacillus plantarum* DSM 26329, hereinafter also named "MP2026" and "*Lactobacillus plantarum* MP2026". According to the Budapest Agreement, all restrictions on the availability to the public of the material so deposited will be irrevocably removed upon the granting of a patent.

In one aspect, the invention relates to a composition comprising at least one of said strains or their analogues or functionally equivalent strains thereof, and if necessary other ingredients or additives. Furthermore, the composition can be used for the preparation of a pharmaceutical product for human or veterinary use preferably for treating lactose intolerance and malabsorption, fructose intolerance and malabsorption, and bloating.

Pharmaceutical products contain an effective amount of the composition together with adequate amounts of pharmaceutically or veterinary acceptable excipients. In this regard, the pharmaceutical product may be prepared in any suitable form which does not negatively affect bioavailability of the strains forming the composition of the invention. Thus, the composition of the invention can be formulated to be administered orally in the form of, for instance, freeze-dried powder, capsules, liquid preparations, etc. Selection of the excipients and most appropriate methods for formulation can be performed by the person skilled in the art, taking into account the particular purpose of the composition. Oral administration is preferred, however the composition can also be administered rectally, topically, enterally or as injection.

The beneficial properties of pharmaceutical compositions containing at least one of said strains may be further enhanced by addition of other probiotic strains.

Many probiotics are used for the manufacture of food or feed products; consequently a further important aspect of the invention is provision of a human food or animal feed composition comprising at least one of said strains or their analogues or functionally equivalent strains thereof.

When preparing such food or feed products manufacturers usually make use of a so-called starter culture being cultures used to process food and feed products. Starter cultures are widely used in dairy industry. Typically, starter cultures impart specific features to various food or feed products. Thus a further aspect of the present invention is a starter culture composition comprising at least one of said strains or their analogues or functionally equivalent strains thereto, preferably wherein the starter culture composition has a concentration of viable cells, which is in the range of $10^4$ to $10^{14}$ CFU per gram of the composition.

DESCRIPTION OF THE INVENTION

Strains of the genus *Lactobacillus* are readily isolated from different sources, such as animal intestine, skin or faeces, traditional foods of plant or animal origin, etc. Normally, the metabolic pathways of the isolated strains are optimized for an efficient consumption of carbon sources present in their environment. Surprisingly, in sour turnip a *Lactobacillus* strain has been identified which is capable of consuming sugars from different sources, namely fructose from fruits, lactose from milk and raffinose from vegetables, all at very high efficiency. This invention thus refers to new strains of *Lactobacillus* having the ability to consume fructose, lactose and raffinose with a rate similar to that at which they consume glucose whereby the consumption of these sugars does not lead to generation of substantial amounts of gas.

The procedure to isolate such strains of *Lactobacillus* was carried out as follows: liquid from sour turnip was serially diluted and plated onto MRS agar plates. Single colonies were obtained, cultivated in liquid MRS medium and cultures stored in 30% glycerol (see Example 1 and Example 2). Cultures of newly isolated strains as well as some commercially available probiotic strains were then tested for production of gas during cultivation in liquid MRS medium using Durham tubes (see Example 3).

The cultures which were found not to produce a substantial amount of gas were then cultivated in MRS medium with 2% glucose as well as in the variants of the MRS medium, in which glucose was replaced by 2% fructose, lactose or raffinose and in the variant where water was added instead of glucose (see Example 4). Cultivation was carried out in 96-well plates at 37° C. in microaerobic conditions and OD at 600 nm (OD600) of the cultures was followed by a spectrophotometer. Cultures, in which the increase of OD600 was comparable in the presence of fructose, lactose or raffinose to the increase in the presence of glucose, were elected for further testing. The ratio of growth rates on fructose, lactose and raffinose of at least 0.7 compared to the growth rate on glucose was considered as suitable (Table 1). Additionally, the strains were also cultivated in a modified MRS medium with 25% nitrogen sources (0.25% peptone, 0.125% yeast extract, 0.1% Tween 80, 0.2% $K_2HPO_4$, 0.5% Na-acetate, 0.2% $(NH_4)_2$ citrate, 0.02% $MgSO_4.7H_2O$, 0.005% $MnSO_4.H_2O$, 2% glucose, pH 6.4). Likewise, the strains with a growth rate on low-nitrogen medium of at least 0.7 of the growth rate in original MRS were considered suitable, because it is known that nitrogen concentration in the intestine can be very low. Importantly, the strain *Lactobacillus plantarum* KR6 DSM 27870 (at the time named "KR6") was identified as one of the strains with an optimum growth rate on fructose (88% of the rate on glucose), lactose (85% of growth on glucose) and raffinose (77% of growth on glucose) as well as in low nitrogen conditions (83.7% of growth rate in normal MRS). In contrast, the commercially available strain *Lactobacillus plantarum* 299v (EP0554418) showed a poor growth rate on raffinose (21% of the rate on glucose). Similarly, *Lactobacillus plantarum* B-4496 showed a non-optimal growth rate on lactose (on average 55% of the growth on glucose). The growth rates of several previously known and newly isolated strains in different media are presented in Table 1. It can be clearly observed that a great majority of strains do not grow on at least one of the tested sugars. Among the strains presented in Table 1, *Lactobacillus plantarum* KR6 was the one which showed optimum growth on fructose, lactose and raffinose while at the same time possessing other suitable properties of probiotic strains, as described in continuation.

In the next step the cultures were tested for survival in conditions resembling the passage through the human intestinal tract (see Example 5). This is an important feature when considering the use of *Lactobacillus* strains as probiotics. The strain *Lactobacillus plantarum* DSM 27870 (at the time named "KR6") showed a reasonable resistance to conditions of human intestinal tract.

Importantly, the strains that can be used as probiotics for human consumption have to be devoid of antibiotic resistance markers. Therefore in the next step the strains showing favourable sugar consumption features were tested for resistance to a list of selected antibiotics: ampicillin, gentamicin, kanamycin, streptomycin, erythromycin, clindamycin, tetracycline, chloramphenicol and quinupristin+dalfopristin (see Example 6). The strain *Lactobacillus plantarum* DSM 27870 (at the time named "KR6") was found not to be resistant to any of said antibiotics.

In order to further characterize the strain named "KR6" we isolated the genomic DNA (see Example 8) and carried out genome sequencing using the 454 pyrosequencing method. Based on the sequence of 16S RNA gene the strain KR6 was classified as *Lactobacillus plantarum* species (see Example 9).

It is a known characteristic of most microbial strains that in the presence of several nutrients they will first consume the preferred nutrient almost exclusively. Only after the preferred nutrient is consumed, the culture will start consuming other nutrients.

Most often the preferred nutrient of microorganisms is glucose which is also the case for *Lactobacillus plantarum* DSM 27870. Therefore, in order to further improve the properties of *Lactobacillus plantarum* DSM 27870 we aimed to obtain mutant strains which would no longer show preferential consumption of glucose but would consume fructose, lactose and raffinose also in the presence of glucose. Therefore, we obtained mutant strains which were resistant to 2-deoxyglucose and screed 2-deoxyglucose-resistant mutants for consumptions of fructose, lactose and raffinose in the MRS medium, in which both glucose and one of three said sugars were present (see Example 7). The strains that were observed to consume fructose, lactose and raffinose in the MRS medium, in which glucose was also present, were considered to have deregulated carbon catabolite repression. Among those mutants the strain *Lactobacillus plantarum* DSM 26329 was selected.

It is clear that using the deposited strains as starting material the person skilled in the art can use conventional mutagenesis or reisolation techniques to obtain further mutants or derivatives thereof that retain or enhance the herein described relevant features and advantages of the strains *Lactobacillus plantarum* DSM 27870 and *Lactobacillus plantarum* DSM 26329. The person skilled in the art will also know to select methods, similar to examples shown below, to determine the metabolic potential of mutant strains and their suitability for use in compositions for probiotic use.

When the strains of the invention or compositions containing these strains or products containing these strains are consumed by people or animals who feel discomfort or pain when eating food containing lactose, fructose or raffinose, the non-absorbed sugars will be partially consumed by said strains.

It is clear from the above that the strains of this invention can be useful in the preparation of a composition which can be further used for the preparation of pharmaceutical and veterinary products for the treatment of lactose intolerance and malabsorption, fructose intolerance and malabsorption, and bloating.

The composition contains an effective amount of at least one of the strains of the invention or their analogues or functionally equivalent strains thereof, and if necessary other ingredients and additives. This composition can be used for the preparation of pharmaceutical products for human or veterinary use, human food or animal feed.

Pharmaceutical products contain an effective amount of the composition together with adequate amounts of pharmaceutically or veterinary acceptable excipients. In this regard, the pharmaceutical product may be prepared in any suitable form which does not negatively affect bioavailability of the strains forming the composition of the invention. Thus, the composition of the invention can be formulated to be administered orally in the form of, for instance, freeze-dried powder, capsules, liquid preparations, etc. Selection of excipients and most appropriate methods for formulation can be performed by the person skilled in the art, taking into account the particular purpose of the composition. Oral administration is preferred, however the composition can also be administered rectally, topically, enterally or as injection.

The beneficial properties of compositions containing said strains may be further enhanced by addition of other probiotic strains.

Many probiotics are used for the manufacture of food or feed products; consequently a further important aspect of the invention is the provision of a human food or animal feed composition comprising at least one of said strains or their analogues or functionally equivalent strains thereof. Preferably, the strains of the invention or composition of the invention may be administered as a supplement to normal diet or as a component of a nutritionally complete human food or animal feed. The dosage form may be liquid or solid. In the latter case, the product may be powdered and formed into tablets, granules or capsules or simply mixed with other food ingredients to form functional food.

The human food or animal feed composition or dosage form should comprise at least one of the strains of this invention or their analogues or functionally equivalent strains thereof, as described above, so that the amount of each of the strains that is available for an individual is about $10^3$-$10^{14}$ CFU per day, such as $10^6$-$10^{13}$ CFU per day including $10^8$-$10^{12}$ CFU per day or even $10^9$-$10^{11}$ CFU per day. This amount depends on an individual's weight, and it is preferably about $10^9$-$10^{12}$ CFU/day for humans and $10^7$-$10^{10}$ CFU/day for animal. It will be understood, however, that a specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

Microorganisms are involved in the manufacturing of food and feed products including most dairy products. Various bacterial cultures, in particular cultures of bacteria generally classified as lactic acid bacteria, are essential in the making of all fermented milk products, cheese and butter. Cultures of these microorganisms are often referred to as starter cultures and impart specific features to various dairy products by performing a number of functions. In order for the starter culture to exert its function it is essential that it comprises live cells in sufficient amounts. Thus one embodiment of the present invention is a starter culture composition comprising at least one of said strains or their analogues or functionally equivalent strains thereof, preferably wherein the starter culture composition has a concentration of viable cells, which is in the range of $10^4$ to $10^{14}$ CFU per gram of the composition.

Starter cultures are typically used for the manufacturing a food or feed product by adding the starter culture composition to a food or feed product starting material and keeping thus inoculated starting material under conditions where the lactic acid bacterium is metabolically active. In a preferred embodiment the food product is a milk-based product such as cheese, yoghurt, butter or a liquid fermented milk product, such as buttermilk or drinking yoghurt.

The following Examples are for illustrative purposes only and are not intended to limit the invention.

EXAMPLES

Example 1: Cultivation of *Lactobacillus* Strains

For stock preparation and liquid cultures MRS medium (1% peptone, 1% beef extract, 0.5% yeast extract, 2% glucose, 0.1% Tween 80, 0.2% $K_2HPO_4$, 0.5% Na-acetate, 0.2% $(NH_4)_2$ citrate, 0.02% $MgSO_4.7H_2O$, 0.005% $MnSO_4.H_2O$, pH=6.4) was used. Stock (1% v/v) of *Lactobacillus* strain was inoculated and cultivated for 14 to 18 h at 37° C. in microaerophilic conditions. The culture was centrifuged at 3000 r/min for 5 min. Supernatant was removed and pellet resuspended in MRS with 30% glycerol and stored at −80° C.

Example 2: Isolation of *Lactobacillus* Strains from Sour Turnip

Liquid from sour turnip was used for serial dilutions in a sterile saline solution. Dilutions were plated on MRS agar plates (1% peptone, 1% beef extract, 0.5% yeast extract, 2% glucose, 0.1% Tween 80, 0.2% $K_2HPO_4$, 0.5% Na-acetate, 0.2% (NH$_4$)$_2$ citrate, 0.02% MgSO$_4$.7H$_2$O, 0.005% MnSO$_4$.H$_2$O, 1.5% agar, pH=6.4) and incubated at 37° C. for 48 hours in a plastic box with GENbox anaer (bioMerieux). All the white round colonies were spread to single colonies on fresh MRS agar plates and the liquid MRS medium was inoculated with single colonies. Cells were recovered by centrifugation and resuspended in MRS with 30% glycerol for storage.

Example 3: Selection of Strains for Gas Production

Strains were first tested for production of gas during growth with Durham tubes. Test tubes were filled with 7 ml of MRS medium. Durham tubes were inserted and autoclaved. Durham tubes were filled with medium during sterilization. If bacteria produced gas during growth, a bubble was captured in Durham tube. Strains were inoculated (1% v/v) and checked for gas production after 12 to 18 hours. No gas production during growth was desired.

Figure 1:
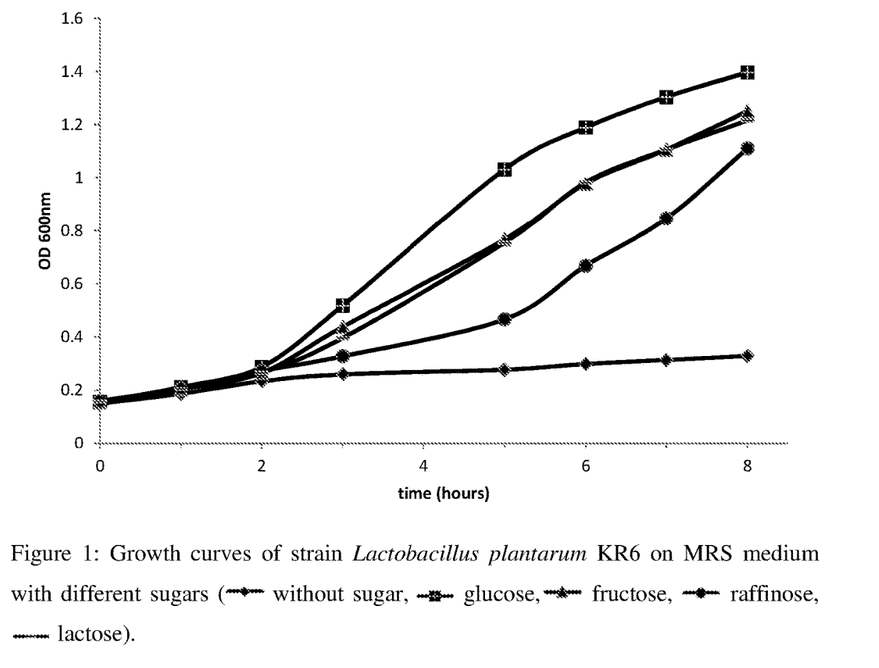
FIG. 1. The graph represents a change in optical density (OD) over time for the strain KR6 in MRS-based growth media containing different sugars or no sugar. The obtained growth curves show a comparable growth of the KR6 strain in different media.

Example 4: Selection of Strains for Sugar Consumption and Rapid Growth in Conditions of Low Concentration of Nitrogen Sources Different strains were inoculated (1% v/v) in 10 ml of MRS medium in a 15 ml falcon tube which was maintained at 37° C. overnight in microaerophilic conditions. Tubes were centrifugated and pellet resuspended in a sterile saline solution. Modified MRS medium (1% peptone, 0.5% yeast extract, 0.1% Tween 80, 0.2% K$_2$HPO$_4$, 0.5% Na-acetate, 0.2% (NH$_4$)$_2$ citrate, 0.02% MgSO$_4$.7H$_2$O, 0.005% MnSO$_4$.H$_2$O, pH 6.4) was mixed with different sugars (2%). Glucose, raffinose, lactose and fructose were used and as control the sugar was replaced with sterile water. Medium was distributed into 96-well microtiter plates, 190 µl in single well. Each well was inoculated with 10 µl of overnight culture in a sterile saline solution. Microtiter plates were kept at 37° C. and OD 600 nm was measured each hour. Growth curves were drawn and growth on each sugar was compared (FIG. 1). Good growth on raffinose, lactose and fructose was desired (Table 1). All the strains with gas production on glucose and strains with an inefficient consumption of sugars were eliminated from further tests.

In order to test the ability of the tested strains for a rapid growth in conditions of low concentration of nitrogen source, we additionally cultivated the strains in conditions of low concentration of nitrogen sources. The experiment was carried out as described in the paragraph above, using the modified MRS medium with 25% nitrogen sources (0.25% peptone, 0.125% yeast extract, 0.1% Tween 80, 0.2% K$_2$HPO$_4$, 0.5% Na-acetate, 0.2% (NH$_4$)$_2$ citrate, 0.02% MgSO$_4$.7H$_2$O, 0.005% MnSO$_4$.H$_2$O, 2% glucose, pH 6.4). The results are presented in Table 1, column 6 (25% nitrogen source).

TABLE 1

Growth rate of different strains in MRS medium without sugar addition, with addition of fructose, raffinose or lactose (expressed as % of growth rate on glucose) and in conditions of low concentration of nitrogen sources is displayed. Gas production during growth on glucose is indicated (+ gas production, − no gas production).

| Strain | No sugar (%) | Fructose (%) | Raffinose (%) | Lactose (%) | 25% nitrogen source (%) | Gas production during growth on glucose |
| --- | --- | --- | --- | --- | --- | --- |
| Bifidobacterium animalis subsp. lactis BB12 | 5.6 | 77.5 | 46.6 | 12.2 | 79.8 | − |
| Bifidobacterium bifidum B-41410 | 8.1 | 93.5 | 11.7 | 56.4 | 66.3 | − |
| Bifidobacterium breve B-41408 | 18.6 | 93.8 | 25.8 | 84.8 | 83.8 | − |
| Bifidobacterium infantis B-41661 | 8.7 | 79.3 | 11.3 | 38.2 | 68.6 | − |
| Bifidobacterium longum B-41409 | 10.1 | 89.7 | 15.4 | 27.9 | 71.3 | − |
| Lactobacillus acidophilus B-4495 | 13.7 | 84.7 | 97.1 | 99.4 | 64.3 | − |
| Lactobacillus acidophilus LA-5 | 26.9 | 53.9 | 49.2 | 91.5 | 35.9 | − |
| Lactobacillus brevis B-3065 | 47.7 | 98.4 | 51.0 | 61.5 | 62.3 | + |
| Lactobacillus casei subsp. casei B-441 | 105 | 91.9 | 18.5 | 29.8 | 76.3 | − |
| Lactobacillus delbrueckii subsp. bulgaricus B-548 | 9.6 | 88.8 | 14.5 | 50.2 | 69.5 | − |
| Lactobacillus helveticus B-4526 | 40.8 | 82.3 | 38.4 | 74.4 | 85.8 | − |
| Lactobacillus johonii B-2178 | 6.5 | 30.2 | 9.8 | 47.6 | 82.0 | − |
| Lactobacillus paracasei sub. paracasei B-4560 | 17.1 | 91.3 | 23.2 | 78.9 | 84.6 | − |
| Lactobacillus paracasei subsp. paracasei DSM 20207 | 17.7 | 89.8 | 22.5 | 81.4 | 67.1 | − |

TABLE 1-continued

Growth rate of different strains in MRS medium without sugar addition, with addition of fructose, raffinose or lactose (expressed as % of growth rate on glucose) and in conditions of low concentration of nitrogen sources is displayed. Gas production during growth on glucose is indicated (+ gas production, − no gas production).

| Strain | No sugar (%) | Fructose (%) | Raffinose (%) | Lactose (%) | 25% nitrogen source (%) | Gas production during growth on glucose |
|---|---|---|---|---|---|---|
| *Lactobacillus plantarum* B-4496 | 14.8 | 72.0 | 87.7 | 54.6 | 89.7 | − |
| *Lactobacillus plantarum* 299v | 16.7 | 79.2 | 21.4 | 95.5 | 86.3 | − |
| *Lactobacillus reuteri* DSM 20016 | 19.3 | 18.4 | 88.1 | 74.9 | 28.7 | + |
| *Lactobacillus reuteri* Protectis | 12.8 | 16.6 | 97.8 | 105.6 | 84.1 | + |
| *Lactobacillus rhamnosus* B-442 | 18.8 | 92.3 | 24.3 | 80.5 | 72.1 | − |
| *Lactobacillus rhamnosus* LGG | 9.8 | 88.0 | 12.7 | 15.9 | 54.2 | − |
| *Lactobacillus sakei* DSM 20100 | 44.5 | 72.4 | 49.7 | 44.6 | 37.1 | − |
| *Lactobacillus sakei* DSM 20101 | 28.9 | 91.3 | 34.7 | 41.1 | 78.3 | − |
| *Lactobacillus salivarius* subsp. *salicinius* B-1950 | 10.3 | 97.5 | 106.3 | 110.8 | 15.5 | − |
| KZ1 | 9.9 | 89.1 | 13.7 | 15.4 | 64.0 | − |
| KZ2 | 10.5 | 89.5 | 12.9 | 14.7 | 67.9 | − |
| KZ3 | 13.7 | 65.7 | 21.6 | 68.4 | 70.9 | − |
| KZ4 | 11.3 | 95.9 | 13.9 | 16.0 | 66.1 | − |
| KZ5 | 7.0 | 81.4 | 9.9 | 14.5 | 56.5 | − |
| *Lactobacillus casei* KZ6 | 8.5 | 87.5 | 20.6 | 18.6 | 62.1 | − |
| KZ7 | 18.4 | 101.0 | 99.4 | 101.1 | 95.3 | + |
| KZ8 | 19.3 | 102.1 | 98.5 | 100.3 | 95.6 | + |
| KZ9 | 18.1 | 101.4 | 97.0 | 97.3 | 94.3 | + |
| KZ10 | 16.8 | 101.5 | 97.0 | 98.2 | 95.1 | + |
| KR1 | 15.8 | 72.1 | 25.4 | 74.0 | 76.4 | − |
| KR2 | 26.6 | 109.8 | 30.3 | 39.6 | 79.5 | + |
| *Lactobacillus plantarum* KR3 | 8 | 62 | 54 | 93 | 56.5 | − |
| KR4 | 56.5 | 152.0 | 58.0 | 59.1 | 51.2 | + |
| KR5 | 20.0 | 95.3 | 20.7 | 21.3 | 71.2 | + |
| *Lactobacillus plantarum* KR6 | 12.0 | 88.0 | 77.0 | 85.0 | 83.7 | − |
| KR7 | 14.4 | 70.7 | 17.3 | 70.2 | 70.8 | − |
| KR8 | 16.0 | 103.0 | 96.5 | 96.9 | 95.3 | + |
| KR9 | 15.7 | 101.3 | 97.2 | 97.7 | 96.1 | + |
| KR10 | 15.9 | 99.3 | 94.8 | 96.7 | 93.8 | + |
| KR11 | 18.6 | 102.6 | 98.0 | 97.8 | 94.0 | + |
| KR12 | 17.6 | 103.4 | 97.4 | 97.9 | 93.4 | + |
| KM1 | 13.7 | 67.9 | 18.2 | 89.7 | 76.7 | − |
| KM2 | 16.8 | 76.0 | 19.1 | 92.2 | 84.3 | − |
| KM3 | 16.6 | 92.4 | 21.4 | 90.9 | 61.1 | − |
| KM4 | 18.2 | 80.7 | 20.8 | 90.4 | 84.3 | − |
| KM5 | 16.7 | 62.2 | 21.4 | 92.6 | 84.9 | − |
| KM6 | 18.0 | 69.2 | 32.2 | 97.2 | 84.7 | − |
| KM7 | 13.0 | 62.8 | 19.6 | 98.4 | 84.9 | − |
| KM8 | 17.4 | 70.8 | 15.3 | 89.9 | 82.5 | − |
| KM9 | 12.4 | 79.2 | 6.2 | 88.5 | 50.3 | − |
| KM10 | 13.5 | 96.7 | 6.2 | 91.9 | 54.2 | − |
| KM11 | 21.7 | 91.9 | 15.9 | 82.1 | 57.5 | − |
| KM12 | 14.9 | 86.0 | 14.6 | 13.7 | 79.7 | + |

Example 5: Survival on Simulated Gastric and Intestinal Conditions

Survival testing of simulated gastric and intestinal conditions was done to determine survival in passage through the digestive system. Overnight cultures (10 ml) were centrifugated (3000 r/min, 3 min) and cells resuspended in 3 ml of a sterile saline solution. With 1 ml of solution, 50 ml of simulated gastric juice (125 mmol/l NaCl, 7 mmol/l KCl, 45 mmol/l, 3 g/l pepsine) was inoculated with different pH (2.4, 3 or 7). Samples were taken 0, 90 or 180 min after incubation and serial dilutions plated on MRS agar. After 3 hours the cells were collected with centrifugation and resuspended in simulated intestinal juice (0.1% pancreatin, 0.3% bile salts, pH 8). Samples were taken and enumerated with plating on MRS agar after 0, 90 and 180 minutes. Good survival on low pH and intestinal juice was desired.

Example 6: Antibiotic Resistance

Minimal inhibition concentrations (MIC) were determined for antibiotics required from EFSA (ampicillin (AM), gentamicin (GM), kanamycin (KM), streptomycin (SM), erythromycin (EM), clindamycin (CM), chloramphenicol (CL), quinupristin+dalfopristin (QDA) and tetracycline (TC)). Agar plates consisting of 90% Mueller Hinton Agar (0.2% beef extract, 1.75% acid digest of casein, 0.15% starch, 1.7% agar) and 10% MRS agar with pH adjusted to 6.7, containing 25 ml of medium on petri dish (radius 9 cm) were first dried. Cells from overnight cultures were collected with centrifugation and resuspended in a sterile saline solution to reach OD 600 nm about 0.3. On each plate 100 µl of suspension was spread with sterile cotton bud. One E-Test® (bioMerieux) was placed on each plate. Plates were incubated for 48 hours at 37° C. in anaerobic conditions and results were interpreted following manufacturer's instructions (Table 2). All the strains resistant to at least one antibiotic were eliminated from further tests. All the results were revaluated and KR6 was chosen for mutagenesis and improvement.

above. The best colony was chosen for further adjustment (*Lactobacillus plantarum* MP-10).

EMS mutagenesis was done on the best UV mutant colony (MP-10) with 9% ethyl methanesulfonate. Overnight culture was washed three times with a sterile saline solution and diluted until value OD 600 nm was 0.2. 810 µl of sterile 0.1 M phosphate buffer (pH 7) was mixed with 90 µl of EMS and 100 µl of cell culture with appropriate OD value. Serial dilutions were made after 2 hours and plated on MRS plates medium (1% peptone, 0.5% yeast extract, 0.1% Tween 80, 0.2% $K_2HPO_4$, 0.5% Na-acetate, 0.2% $(NH_4)_2$ citrate, 0.02% $MgSO_4.7H_2O$, 0.005% $MnSO_4.H_2O$, 1.5% agar, pH 6.4) with 10 mM 2-deoxy-D-glucose and 10 g/l lactose. Colonies were replated on same plates and stored in MRS with 30% glycerol. Colonies were tested for carbohydrate digestion (Table 3). Overnight culture was inoculated in MRS liquid medium (5% v/v) which contained all four sugars (glucose, fructose, raffinose and lactose) in 4 g/l concentration. After 4 and 8 hours samples were taken, heated at 80° C. for 30 minutes, centrifugated and in supernatant concentrations of sugars were measured (Table 4). Also all the tests from before were done on selected strains. The desired strain should consume all sugars at the same time. Strain *Lactobacillus plantarum* MP-2026 was selected.

TABLE 2

Minimal inhibition concentration (MIC) values for selected strains are displayed. Values in bold exceed MIC values determined by EFSA (AM = 4 mg/l, GM = 32 mg/l, KM = 64 mg/l, SM = 64 mg/l, EM = 1 mg/l, CM = 1 mg/l, QDA = 4 mg/l, TC = 32 mg/l, CL = 8 mg/l) and are considered as resistant. Tetracycline MIC was determined only for non-resistant strains.

| Species | Strain | AM | GM | KM | SM | EM | CM | QDA | TC | CL |
|---|---|---|---|---|---|---|---|---|---|---|
| *Lactobacillus plantarum* | KR6 | 0.19 | 2 | 64 | 64 | 0.25 | 0.38 | 0.75 | 24 | 6 |
| *Lactobacillus plantarum* | B-4496 | 0.19 | 2 | 64 | 64 | 0.5 | 0.25 | 0.5 | 12 | 4 |
| *Lactobacillus acidophilus* | B-4495 | >256 | 1.5 | 32 | 8 | 0.047 | 2 | 0.5 | | 0.5 |
| *Lactobacillus salivarius* subsp. *salicinius* | B-1950 | 0.125 | 4 | >256 | 64 | 0.125 | 0.38 | 0.38 | | 4 |
| *Lactobacillus helveticus* | B-4526 | 2 | 12 | >256 | 128 | 0.19 | 0.125 | 4 | | 3 |
| *Lactobacillus plantarum* | KR3 | 0.19 | 1.5 | 32 | 48 | 1 | 1 | 0.75 | 10 | 6 |
| *Lactobacillus sakei* | DSM 20101 | 0.75 | 2 | 16 | 32 | 0.125 | 0.064 | 0.38 | | 4 |
| *Lactobacillus casei* | KZ6 | 0.75 | 8 | >256 | 64 | 0.064 | 0.094 | 0.75 | | 2 |
| *Lactobacillus sakei* | DSM 20100 | 1 | 8 | 8 | 16 | 0.19 | 0.094 | 2 | 1.5 | 3 |

Example 7: Mutagenesis and Selection of Mutants

UV mutagenesis was done on *Lactobacillus plantarum* KR6 to improve survival in simulated gastric and intestinal conditions described above. Overnight culture was washed three times with a sterile saline solution. For UV treatment 2 ml culture was mixed with 18 ml of saline solution and exposed to UV light (254 nm) for 2 minutes. The distance between the light and the culture was 35 cm. Serial dilutions were plated on MRS agar. Plates were kept in the dark and incubated at 37° C. for 48 hours. Single colonies were chosen, stored in 30% glycerol with MRS and tested for survival in simulated gastric and intestinal juice as described

TABLE 3

Growth rate of different strains in MRS medium without sugar addition and with addition of fructose, raffinose or lactose (expressed as % of growth rate on glucose) is displayed.

| Strain | No sugar (%) | Fructose (%) | Raffinose (%) | Lactose (%) |
|---|---|---|---|---|
| *Lactobacillus plantarum* KR6 | 12.0 | 88.0 | 77.0 | 85.0 |
| *Lactobacillus plantarum* MP-10 (improved survival of | 13.8 | 71.3 | 39.6 | 44.8 |

TABLE 3-continued

Growth rate of different strains in MRS medium without sugar addition and with addition of fructose, raffinose or lactose (expressed as % of growth rate on glucose) is displayed.

| Strain | No sugar (%) | Fructose (%) | Raffinose (%) | Lactose (%) |
|---|---|---|---|---|
| simulated gastric conditions) | | | | |
| Lactobacillus plantarum MP-2026 | 10.5 | 98.2 | 98.0 | 92.1 |

TABLE 4

Remaining concentrations of fructose, glucose, lactose and raffinose after 8- hour cultivation of strains in MRS medium, initially containing all four sugars at concentration of 4 g/l. Two separate experiments were done.

| Strain | Measurement | Fructose | Glucose | Lactose | Raffinose |
|---|---|---|---|---|---|
| Lactobacillus plantarum KR6 | 1. | 0 | 0 | 3.7 | 3.3 |
| | 2. | 0 | 0 | 3.5 | 3.4 |
| Lactobacillus plantarum MP-10 | 1. | 0.3 | 0.4 | 4.3 | 3.7 |
| | 2. | 0.1 | 0.2 | 3.5 | 3.4 |
| Lactobacillus plantarum MP-2026 | 1. | 0.3 | 1.1 | 2.2 | 1.7 |
| | 2. | 0.1 | 1.3 | 3 | 3 |

Example 8: Isolation of Genomic DNA

Stock of *Lactobacillus plantarum* KR6 strain was used (1% v/v) to inoculate 10 ml of MRS medium in a 15 ml falcon tube which was maintained at 37° C. overnight (16 hours) in microaerophilic conditions. Fresh MRS medium was inoculated with 10% of overnight culture to get cells in logarithmic phase of growth. Cultures were grown for 5 hours at 37° C. in microaerophilic conditions. Cells were recovered by centrifugation and genomic DNA was prepared using PureLink Genomic DNA Mini Kit (Invitrogen) according to the instructions of the kit manufacturer with slight modifications. Lyzozyme incubation was prolonged to 45 minutes and all the washing steps were done twice. DNA was resuspended in 100 μl TE buffer.

Example 9: Species Determination of Isolates with 16S Fragment Sequencing

1. PCR with genomic DNA described in previous step was done with primers P1 (5'-GCGGCGTGCCTAATA-CATGC) and P4 (5'-ATCTACGCATTTCACCGC-TAC).
2. PCR product was cleaned from gel with Wizard SV Gel and PCR Clean-Up System (Promega).
3. A-tails were added with DreamTaq polymerase (30 μl cleaned PCR product, 5 μl PCR buffer, 4 μl dNTP, 1 μl DreamTaq polymerase, 72° C., 30 minutes).
4. PCR product was again cleaned the same as in step 2.
5. Ligation was done (2 μl PCR 2.1 vector, 1 μl ligase, 1 μl ligation buffer, 6 μl cleaned PCR product from step 4, overnight 4° C.)
6. Electroporation was done with competent *E. coli* DH10β2 μl of ligation reaction was added to competent cells, electroporated and mixed with 1 ml of 2TY medium and incubated at 37° C. for 45 minutes. Cells are separated with centrifugation (5000 r/min, 3 min) and around 800 μl of supernatant is discarded. The rest is resuspended and spread on 2TY plates with X-gal, IPTG and kanamycin 25 μg/ml. Plates are incubated on 37° C. overnight.
7. Single white colonies are picked for overnight culture on 37° C. in liquid 2TY medium with 100 μg/ml of ampicillin. Plasmids are isolated from the culture and restriction is done with EcoRI. The fragments should be around 700 bp long and 6 fragments of each strain with the right length were sent for sequencing. Sequences were put in BLAST and the species was determined. The sequences of the same strain were also aligned. For strain KR6 species *Lactobacillus plantarum* was determined with 99% similarity.

Part of 16S sequence (634 bp) of strain *Lactobacillus plantarum* KR6:

GCGGCGTGCCTAATACATGCAAGTCGAACGAACTCTGGTATTGATTGGT

GCTTGCATCATGATTTACATTTGAGTGAGTGGCGAACTGGTGAGTAACA

CGTGGGAAACCTGCCCAGAAGCGGGGGATAACACCTGGAAACAGATGCT

AATACCGCATAACAACTTGGACCGCATGGTCCGAGCTTGAAAGATGGCT

TCAGCTATCACTTTTGGATGGTCCCGCGGCGTATTAGCTAGATGGTGGG

GTAACGGCTCACCATGGCAATGATACGTAGCCGACCTGAGAGGGTAATC

GGCCACATTGGGACTGAGACACGGCCCAAACTCCTACGGGAGGCAGCAG

TAGGGAATCTTCCACAATGGACGAAAGTCTGATGGAGCAACGCCGCGTG

AGTGAAGAAGGGTTTCGGCTCGTAAAACTCTGTTGTTAAAGAAGAACAT

ATCTGAGAGTAACTGTTCAGGTATTGACGGTATTTAACCAGAAAGCCAC

GGCTAACTACGTGCCAGCAGCCGCGGTAATACGTAGGTGGCAAGCGTTG

TCCGGATTTATTGGGCGTAAAGCGAGCGCAGGCGGTTTTTTAAGTCTGA

TGTGAAAGCCTTCGGCTCAACCGAAGAAGTGCATCGGAAACTGGGA

The invention claimed is:

1. A *Lactobacillus plantarum* strain having been deposited with Leibniz-Institut DSMZ—Deutsche Sammlung von Mikroorganismen und Zellkulturen GmbH on Oct. 30, 2013 under accession number DSM 26329.

2. A pharmaceutical product for human or veterinary use containing an effective amount of the strain according to claim 1 and one or more pharmaceutically acceptable excipients.

3. A human food or animal feed composition comprising the strain according to claim 1, wherein the composition is a milk-based product.

4. A starter culture composition comprising the strain according to claim 1, wherein the *Lactobacillus* strain is present at a concentration of viable cells in the range of $10^4$ to $10^{14}$ CFU per gram of the composition.

5. A method of treatment of lactose intolerance and malabsorption, fructose intolerance and malabsorption, or bloating comprising:

administering an effective amount of the *Lactobacillus plantarum* strain of claim 1.

6. A method of treatment of lactose intolerance and malabsorption, fructose intolerance and malabsorption, or bloating comprising:

administering an effective amount of the pharmaceutical product of claim 2.

7. A method of treatment of lactose intolerance and malabsorption, fructose intolerance and malabsorption, or bloating comprising:

administering an effective amount of the human food or animal feed composition of claim 3.

8. A method of treatment of lactose intolerance and malabsorption, fructose intolerance and malabsorption, or bloating comprising:

administering an effective amount of the starter culture composition of claim 4.

* * * * *